United States Patent
Krahn et al.

(10) Patent No.: US 7,709,504 B2
(45) Date of Patent: May 4, 2010

(54) USE OF SUBSTITUTED 2-THIO-3,5-DICYANO-4-PHENYL-6-AMINOPYRIDINES IN THE TREATMENT OF NAUSEA AND VOMITING

(75) Inventors: Thomas Krahn, Hagen (DE); Wolfgang Thielemann, Wuppertal (DE); Ulrich Rosentreter, Wuppertal (DE); Nicole Diedrichs, Velbert (DE); Thomas Krämer, Wuppertal (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 26 days.

(21) Appl. No.: 11/631,755

(22) PCT Filed: Jun. 23, 2005

(86) PCT No.: PCT/EP2005/006779

§ 371 (c)(1),
(2), (4) Date: Feb. 20, 2008

(87) PCT Pub. No.: WO2006/002823

PCT Pub. Date: Jan. 12, 2006

(65) Prior Publication Data

US 2008/0249133 A1    Oct. 9, 2008

(30) Foreign Application Priority Data

Jul. 6, 2004    (DE) .................... 10 2004 032 651

(51) Int. Cl.
A61K 31/4418    (2006.01)
A61K 31/4436    (2006.01)
A61K 31/444    (2006.01)

(52) U.S. Cl. ....................... 514/335; 514/342
(58) Field of Classification Search ........................ None
See application file for complete search history.

(56) References Cited

U.S. PATENT DOCUMENTS 7,045,631 B2    5/2006   Rosentreter et al. ......... 546/261
7,078,417 B2 *  7/2006   Rosentreter et al. ......... 514/333

FOREIGN PATENT DOCUMENTS

WO    03008384    1/2003
WO    03053441    3/2003

OTHER PUBLICATIONS

Vippagunta et al., Advanced Drug Delivery Reviews, 48 (2001), pp. 3-26.*
Sarna et al., Gastroenterology Clinics in North America, 18(2) (Jun. 1989), 373-404.*

* cited by examiner

*Primary Examiner*—Phyllis G. Spivack
(74) *Attorney, Agent, or Firm*—Edwards Angell Palmer & Dodge LLP; Weiying Yang; Ralph A. Loren

(57) ABSTRACT

The present invention relates to the use of substituted 2-thio-3,5-dicyano-4-phenyl-6-amino-pyridines of the formula (I)

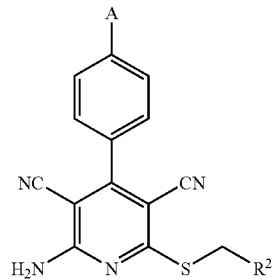

wherein the terms A and $R^2$ are herein defined, for treatment of nausea and vomiting.

4 Claims, No Drawings

USE OF SUBSTITUTED 2-THIO-3,5-DICYANO-4-PHENYL-6-AMINOPYRIDINES IN THE TREATMENT OF NAUSEA AND VOMITING

The present invention relates to the use of substituted 2-thio-3,5-dicyano4-phenyl-6-amino-pyridines of the formula (I) for production of a medicament for the treatment of nausea and vomiting.

It is known that both adenosine phosphates and adenosine itself in general lead to a more rapid recovery of patients when they are administered after anesthesia. It is observed here that patients treated in this way also suffer less from nausea and vomiting.

Nausea and vomiting can be caused, inter alia, by a medicinal therapy, for example chemotherapy for the treatment of tumors with alkylating substances such as, for example, altretamine, busulfan, carmustine, chlorambucil, cyclophosphamide, cytoxan, dacarbazine, estramustine phosphate, fotemustin, ifosfamide, lomustine, melphalan, miltefosine, nimustine, procarbazine, streptozocin, temozolomide, thiotepa and trofosfamide; with cytotoxic antibiotics such as, for example, azacitidine, bleomycin, dactinomycin, daunorubicin, doxorubicin, epirubicin, idarubicin, mitomycin, mitoxantrone, neocarzinostatin, pirarubicin and valrubicin; with antimetabolites such as, for example, capecitabin, carmofur, cladribine, clofarabine, cytarabine, decarbazine, doxifluridine, floxuridine, fludarabine phosphate, fluorouracil, folic acid, gemcitabine, leucovorin, masoprocol, mercaptopurine, methotrexate, pemeterxed, pentostatin, raltitrexed and tegafur; with alkaloids such as, for example, docetaxel, etoposide, irinotecan, paclitaxel, teniposide, topetecan, topotecan, vinblastine, vincristine, vindesine and vinorelbine; or with other chemotherapeutics such as, for example, carboplatin, cisplatin, hydroxyurea, lobaplatin, nedaplatin and oxaliplatin, and combinations of these; in the chemotherapy of bacterial infections with sulfonamide antibiotics such as, for example, sulfamethoxazole and sulfisoxazole; with macrolide antibiotics such as, for example, erythromycin, azithromycin, clarithromycin and dirithromycin; with fluoroquinolone antibiotics such as, for example, ciprofloxacin, levofloxacin and gatifloxacin; with oxazolidinone antibiotics such as, for example, linezolide; in the chemotherapy of viral infections with antiviral active compounds such as, for example, abacavir, didanosine, emtricitabin, indinavir, tenofovir, zalacitabine, zidovudine, delaviridine, amprenavir, fosamprenavir, lopinavir, nelfinavir, ritonavir, saquinavir, stavudine and acyclovir; or in the therapy of depressions with monoamine oxidase inhibitors such as, for example, selegiline, iso-carboxazide and tranylcypromine sulfate; in the treatment of respiratory diseases such as COPD with inhibitors of the enzyme PDE 4 such as, for example, cilomilast or roflumilast; by the irradiation syndrome, radiotherapy, irradiation of the thorax or lower abdomen, such as, for example, in the treatment of cancer; by poisons and poisonous substances, such as can arise, for example, by metabolic diseases or infections (e.g. inflammation of the gastric mucosa); in pregnancy; by vestibular disorders such as, for example, motion sickness or vertigo, by nausea following an operation, and gastrointestinal blockage; reduced gastrointestinal activity, by visceral pain, such as, for example, in cardiac infarct or peritonitis; by migraine; by increased or reduced intracranial pressure such as, for example, in altitude sickness and by opioid analgesics such as morphine.

In WO 02/069982 A1, the antiemetic action of A1 agonists, preferably of partial A1 agonists, is described by example of adenosine-analogous structures.

Surprisingly, it has now been found that both specific and nonspecific non-adenosine-analogous adenosine agonists are suitable for production of medicaments for the treatment of nausea and vomiting in mammals, in particular in man.

This preferably applies for the compounds of the formula (I), whose preparation and use as medicaments, in particular for the treatment of cardiovascular diseases, has been described in detail in WO 03/053441 and WO 03/008384. The compounds mentioned there in general and especially the compounds specifically mentioned there are an explicit part of the description of the present invention.

The compounds of the formula (I) are both A1-specific (adenosine A1-agonistic action around a factor of 10 greater in comparison to the agonistic effect on the other adenosine receptors, A2a, A2b and A3) and A1-nonspecific (at least a further agonistic effect on one of the other adenosine receptors A2a, A2b or A3, which does not differ by a factor of 10 from the A1-agonistic effect), non-adenosine-analogous adenosine agonists.

The present invention thus relates to the use of compounds of the formula (I)

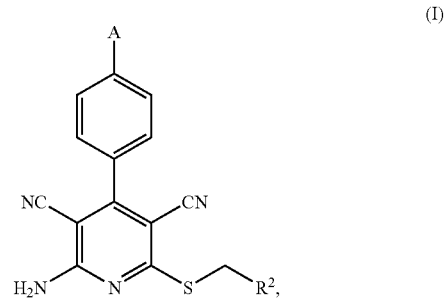

(I)

in which

A is a radical —O—$(CH_2)_n$—O—$R^{1a}$ or —NH—C(=O)—$R^{1b}$, where n is a number 2, 3 or 4, $R^{1a}$ is hydrogen or $(C_1-C_4)$-alkyl, $R^{1b}$ is $(C_1-C_4)$-alkyl, $(C_1-C_4)$-alkoxy, mono- or di-$(C_1-C_4)$-alkylamino, and $R^2$ is pyridyl or thiazolyl, which for its part can be substituted by $(C_1-C_4)$-alkyl, halogen, amino, dimethylamino, acetylamino, guanidino, pyridylamino, thienyl, furyl, imidazolyl, pyridyl, morpholinyl, thiomorpholinyl, piperidinyl, piperazinyl, N—$(C_1-C_4)$-alkylpiperazinyl, pyrrolidinyl, oxazolyl, isoxazolyl, pyrimidinyl, pyrazinyl, thiazolyl optionally substituted by $(C_1-C_4)$-alkyl or phenyl optionally substituted up to three times by halogen, $(C_1-C_4)$-alkyl or $(C_1-C_4)$-alkoxy, and their salts, hydrates, hydrates of the salts and solvates for production of a medicament for the prophylaxis and/or treatment of nausea and vomiting.

The use according to the invention of compounds of the formula (I), in which

A is a radical —O—$(CH_2)_n$—O—$R^{1a}$ or —NH—C(=O)—$R^{1b}$, where n is the number 2, $R^{1a}$ is hydrogen or methyl, $R^{1b}$ is methyl, ethyl, n-propyl, isopropyl, n-butyl, sec-butyl, isobutyl or tert-butyl, and $R^2$ is pyridyl or thiazolyl, which for its part can be substituted by methyl, chlorine, amino, dimethylamino, acetylamino, guanidino, 2-pyridylamino, 4-pyridylamino, thienyl, pyridyl, morpholinyl, 2-methylthiazol-5-yl, phenyl, 4-chlorophenyl or 3,4,5-trimethoxyphenyl, and their salts, hydrates, hydrates of the salts and solvates is preferred.

The use according to the invention of the compound having the following structure (corresponding to Example 6 from WO 03/053441)

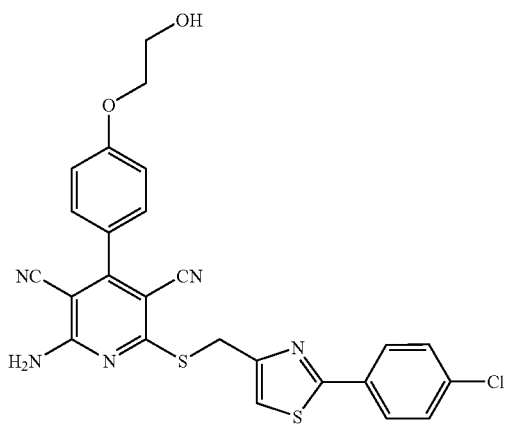

and its salts, hydrates, hydrates of the salts and solvates is particularly preferred.

The use according to the invention of the compound having the following structure (corresponding to Example 1 from WO 03/008384)

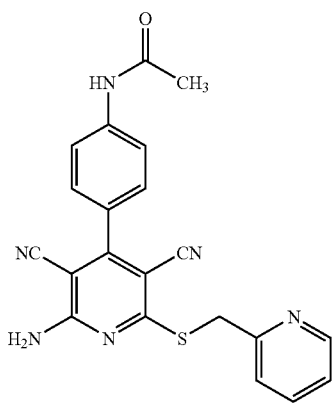

and its salts, hydrates, hydrates of the salts and solvates is likewise particularly preferred.

Depending on the substitution pattern, the compounds of the formula (I) can exist in stereoisomeric forms, which behave either as image and mirror image (enantiomers) or which do not behave as image and mirror image (diastereomers). The invention relates both to the use of the enantiomers or diastereomers and to their respective mixtures. Just like the diastereomers, the racemic forms can be separated into the stereoisomerically uniform constituents in a known manner. Equally, the present invention also relates to the use of the other tautomers of the compounds of the formula (I) and their salts.

Salts of the compounds of the formula (I) can be physiologically acceptable salts of the substances according to the invention with mineral acids, carboxylic acids or sulfonic acids. Particularly preferred salts are, for example, those with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, trifluoroacetic acid, acetic acid, propionic acid, lactic acid, tartaric acid, citric acid, fumaric acid, maleic acid or benzoic acid.

Salts which can be mentioned are also salts with customary bases, such as, for example, alkali metal salts (e.g. sodium or potassium salts), alkaline earth metal salts (e.g. calcium or magnesium salts) or ammonium salts, derived from ammonia or organic amines such as, for example, diethylamine, triethylamine, ethyldiisopropylamine, procaine, dibenzylamine, N-methylmorpholine, dihydroabietylamine, 1-ephenamine or methylpiperidine.

Hydrates or solvates are designated according to the invention as those forms of the compounds of the formula (I) which in the solid or liquid state form a molecular compound or a complex by hydration with water or coordination with solvent molecules. Examples of hydrates are sesquihydrates, monohydrates, dihydrates or trihydrates. Equally, the hydrates or solvates of salts of the compounds according to the invention are also suitable.

Moreover, the invention also comprises the use of prodrugs of the compounds of the formula (I). Prodrugs are designated according to the invention as those forms of the compounds of the formula (I) which can be biologically active or inactive themselves, but can be converted into the corresponding biologically active form under physiological conditions (for example, metabolically or solvolytically).

In the context of the present invention, the substituents, unless stated otherwise, have the following meaning:

Halogen in general represents fluorine, chlorine, bromine or iodine. Fluorine, chlorine or bromine are preferred. Fluorine or chlorine are very particularly preferred.

$(C_1-C_4)$-Alkyl in general represents a straight-chain or branched alkyl radical having 1 to 4 carbon atoms. For example, the following may be mentioned: methyl, ethyl, n-propyl, isopropyl, n-butyl, sec-butyl, isobutyl and tert-butyl.

$(C_1-C_4)$-Alkoxy in general represents a straight-chain or branched alkoxy radical having 1 to 4 carbon atoms. For example, the following may be mentioned: methoxy, ethoxy, n-propoxy, isopropoxy, n-butoxy, sec-butoxy, isobutoxy and tert-butoxy.

Mono- or di-$(C_1-C_4)$-alkylamino in general represents an amino group having one or having two identical or different straight-chain or branched alkyl substituents, which in each case contain 1 to 4 carbon atoms. For example, the following may be mentioned: methylamino, ethylamino, n-propylamino, isopropylamino, t-butylamino, N,N-dimethylamino, N,N-diethylamino, N-ethyl-N-methylamino, N-methyl-N-n-propylamino, N-isopropyl-N-n-propylamino and N-t-butyl-N-methylamino.

The present invention furthermore relates to a method for the prophylaxis and/or treatment of nausea and vomiting using a compound of the formula (I).

In medicinal therapy, the preferred use is prophylaxis (that is substance administration before the patient is exposed to a known stimulus for nausea and vomiting, e.g. chemotherapy, irradiation, full anesthesia).

A further subject of the present invention is a pharmaceutical composition comprising a compound of the formula (I).

All customary administration forms are suitable for the administration of the compounds of the formula (I), i.e. thus orally, parenterally, inhalatively, nasally, sublingually, rectally, locally such as, for example, in implants or stents, or externally such as, for example, transdermally. In the case of parenteral administration, intravenous, intramuscular and subcutaneous administration may be mentioned in particular, e.g. as a subcutaneous depot.

On account of the pharmacokinetic properties of the compounds of the formula (I), their use according to the invention in oral therapy is preferred.

The active compounds can be administered on their own or in the form of preparations. For oral administration, suitable preparations are, inter alia, tablets, capsules, pellets, coated tablets, pills, granules, solid and liquid aerosols, syrups, emulsions, suspensions and solutions. Here, the active compound must be present in an amount such that a therapeutic action is achieved.

The dose and/or formulation is also dependent, inter alia, on the underlying cause, the age and condition of the patient and is finally within the discretion of the physician, pharmacist or veterinarian. In general, the dose to treat an adult human will be in the range from 0.01 to 5000 mg per day, preferably 0.5 to 1000 mg per day. The daily dose can be administered here as an individual dose or in the form of a number of subdoses at appropriate intervals, for example, as two, three, four or more subdoses per day.

According to the treatment active substance, the formulations can here contain between 0.1 and 99% of active compound, suitably 25-95% in the case of tablets and capsules and 1-50% in the case of liquid formulations, i.e. the active compound should be present in amounts which are sufficient in order to achieve the dosage range indicated.

For this purpose, the active compounds can be converted into the customary preparations in a manner known per se. This takes place using inert, nontoxic, pharmaceutically suitable carriers, excipients, solvents, vehicles, emulsifiers and/or dispersants.

Suitable excipients which may be mentioned are, for example: water, nontoxic organic solvents such as, for example, paraffins, vegetable oils (e.g. sesame oil), alcohols (e.g. ethanol, glycerol), glycols (e.g. polyethylene glycol), solid carriers such as natural or synthetic ground minerals (e.g. talc or silicates), sugars (e.g. lactose), emulsifiers, dispersants (e.g. polyvinylpyrrolidone) and glidants (e.g. magnesium sulfate).

In the case of oral administration, tablets can of course also contain additives such as sodium citrate together with additional substances such as starch, gelatin and the like. Aqueous preparations for oral administration can furthermore be treated with flavor enhancers or colorants.

A further subject of the present invention is the use of a combination of one or more compounds of the formula (I) with one or more other active compounds. Suitable combination active compounds are, for example, other active compounds which are suitable for the prophylaxis and/or treatment of nausea and vomiting. By way of example and preferably, its 5HT3 antagonists mentioned such as, for example, ondansetrone, granisetrone, palonosetrone, tropisetrone, ramosetrone. Furthermore, the adenosine agonists described here are suitable for combination with neurokinin antagonists, dopamine antagonists, cannabinoids and other therapies for the prophylaxis and/or treatment of nausea and vomiting.

EXPERIMENTAL SECTION

Emetine-Induced Retching Tests on Ferrets:
The determination of the antiemetic action follows the method described by Gardner et al. in Brit. J. Pharmacol., 116, 3158-3163, 1995.

Sixty minutes before administration of the test substance, the ferrets were accommodated in individual stainless steel cages (40×50×34 cm) having a grid floor. The animals were then treated with emetine (2 mg/kg p.o.) and observed immediately for a period of 2 hours with a view to the following points:
  number of ferrets which show signs of retching and vomiting;
  latency up to initial retching (hours, minutes, seconds);
  latency up to initial vomiting (hours, minutes, seconds);
  retching (how often);
  vomiting (how often);
  number of nauseas;
  average duration of the vomiting periods (minutes, seconds);
  serious side effects on behavior.

Retching is defined according to the invention as a rhythmical respiratory movement against closed vocal cords, while vomiting is defined according to the invention as a forced expulsion of the higher stomach and intestinal contents.

32 ferrets were investigated. The substance tested was administered in two doses, orally sixty minutes before emetine administration, and compared to a control group. Ondansetrone (16 mg/kg p.o.) was given under the same experimental conditions and served as a reference substance.

The 32 ferrets were employed repeatedly in order to investigate 4 test substances. The administration scheme for the three-week experiment looked as follows:
Week 1:
8 ferrets for solvent control
8 ferrets for dose 1 of substance 1
8 ferrets for dose 2 of substance 1
8 ferrets for reference substance
Week 2:
8 ferrets for dose 1 of substance 2
8 ferrets for dose 2 of substance 2
8 ferrets for dose 1 of substance 3
8 ferrets for dose 2 of substance 3
Week 3:
8 ferrets for solvent control
8 ferrets for dose 1 of substance 4
8 ferrets for dose 2 of substance 4
8 ferrets for reference substance The amounts were analyzed and the student's test was used in the comparison of the treated groups with the control group.

The quantitative data were analyzed, Fisher's exact probability test being used for the comparison of the treated groups with the control group.

Result:
The reference substance ondansetrone (16 mg/kg p.o.) has significantly reduced the quantitative occurrence of retching and vomiting (induced by emetine). Emesis was only induced in one of 16 ferrets.

Substance 1 and substance 2 had no significant antiemetic effect on ferrets to which emetine was given in a dose of 0.3 and 3.0 mg/kg p.o. Substance 3 and substance 4, on the other hand, have significantly prevented the emetine-induced vomiting. The administration of 0.3 and 3.0 mg/kg p.o. of substance 4, given 60 minutes before emetine administration, has significantly reduced the quantitative occurrence of retching and vomiting (induced by emetine). Emesis was not induced in any of the ferrets treated with 3.0 mg/kg p.o.

Structures of the Substances 1 to 4:

Substance 1

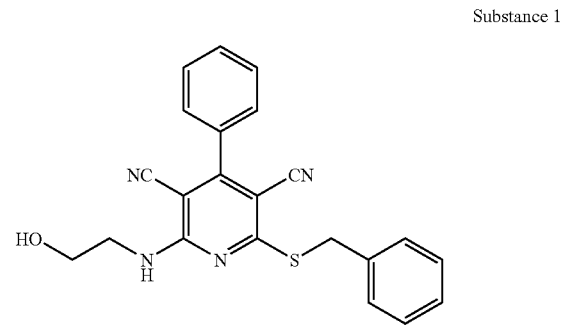

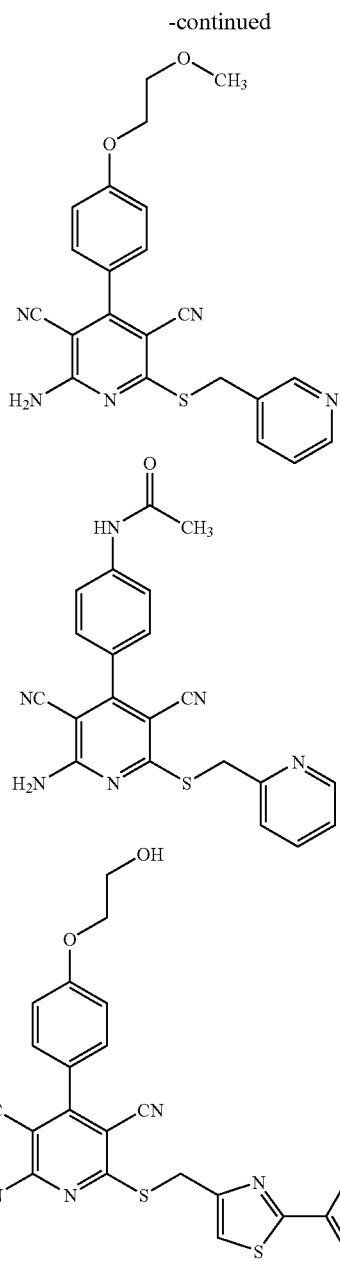

The invention claimed is:

1. A method for the treatment of nausea and vomiting comprising administering a compound of the formula (I)

in which
A is a radical —O—(CH$_2$)$_n$—O—R$^{1a}$ or —NH—C(=O)—R$^{1b}$,
where
n is the number 2,
R$^{1a}$ is hydrogen or methyl,
R$^{1b}$ is methyl, ethyl, n-propyl, isopropyl, n-butyl, sec-butyl, isobutyl or tert-butyl, and
R$^2$ is pyridyl or thiazolyl, wherein the pyridyl or thiazolyl is optionally substituted by methyl, chlorine, amino, dimethylamino, acetylamino, guanidino, 2-pyridylamino, 4-pyridylamino, thienyl, pyridyl, morpholinyl, 2-methylthiazol-5-yl, phenyl, 4-chlorophenyl or 3,4,5-trimethoxyphenyl,
or a salt thereof.

2. The method as claimed in claim 1 wherein the compound of formula (I) is or a salt thereof.

3. The method as claimed in claim 1 wherein the compound of formula (I) is or a salt thereof.

4. The method as claimed in any one of claims 1, 2 and 3 wherein the compound is administered orally.

* * * * *